United States Patent
Pfaff et al.

(10) Patent No.: US 11,773,270 B2
(45) Date of Patent: Oct. 3, 2023

(54) EFFECT PIGMENTS

(71) Applicant: MERCK PATENT GMBH, Darmstadt (DE)

(72) Inventors: Gerhard Pfaff, Muenster (DE); Stephanie Andes, Hanau (DE); Klaus Ambrosius, Dieburg (DE); Ralf Petry, Griesheim (DE); Michael Roesler, Reinheim (DE); Sabine Schoen, Herten (DE)

(73) Assignee: MERCK PATENT GMBH, Darmstadt (DE)

( * ) Notice: Subject to any disclaimer, the term of this patent is extended or adjusted under 35 U.S.C. 154(b) by 40 days.

(21) Appl. No.: 16/921,182

(22) Filed: Jul. 6, 2020

(65) Prior Publication Data

US 2020/0339820 A1    Oct. 29, 2020

Related U.S. Application Data

(63) Continuation of application No. 14/847,726, filed on Sep. 8, 2015, now abandoned, which is a continuation (Continued)

(30) Foreign Application Priority Data

Dec. 21, 2011   (DE) ..................... 10 2011 121 804.5
Jan. 19, 2012   (DE) ..................... 10 2012 000 887.2

(51) Int. Cl.
  *C09C 3/06*   (2006.01)
  *A23G 3/54*   (2006.01)
  (Continued)

(52) U.S. Cl.
  CPC ................ *C09C 3/06* (2013.01); *A23G 3/343* (2013.01); *A23G 3/54* (2013.01); *A23L 5/47* (2016.08);
  (Continued)

(58) Field of Classification Search
  None
  See application file for complete search history.

(56) References Cited

U.S. PATENT DOCUMENTS 6,875,264 B2   4/2005   Zimmermann et al.
6,884,289 B2   4/2005   Schoen
(Continued)

FOREIGN PATENT DOCUMENTS

CN         1738870 A     2/2006
CN       101085882 A    12/2007
(Continued)

OTHER PUBLICATIONS

Gerhard Pfaff and Peter Reynders. "Angle-Dependent Optical Effects Deriving from Submicron Structures of Films and Pigments." Chemical Reviews, vol. 99, 1999, pp. 1963-1981. (Year: 1999).*

(Continued)

*Primary Examiner* — Isaac Shomer
(74) *Attorney, Agent, or Firm* — MILLEN, WHITE, ZELANO AND BRANIGAN, P.C.; Harry B. Shubin (57) ABSTRACT

The present invention relates to effect pigments which are based on flake-form substrates having a circular form factor of 1.2-2 and are coated with at least one high-refractive-index layer, and to the use thereof, inter alia in paints, coatings, printing inks, plastics and in cosmetic formulations.

18 Claims, 1 Drawing Sheet

Related U.S. Application Data of application No. 13/721,212, filed on Dec. 20, 2012, now abandoned.

(51) Int. Cl.

| | | |
|---|---|---|
| *C09D 5/36* | (2006.01) | |
| *C09C 1/00* | (2006.01) | |
| *A61Q 19/00* | (2006.01) | |
| *A61K 8/02* | (2006.01) | |
| *A23G 3/34* | (2006.01) | |
| *C08K 9/02* | (2006.01) | |
| *C09D 11/037* | (2014.01) | |
| *A61Q 3/02* | (2006.01) | |
| *A61Q 19/10* | (2006.01) | |
| *A23L 5/47* | (2016.01) | |

(52) U.S. Cl.
CPC .......... *A61K 8/0258* (2013.01); *A61K 8/0266* (2013.01); *A61Q 3/02* (2013.01); *A61Q 19/00* (2013.01); *A61Q 19/10* (2013.01); *C08K 9/02* (2013.01); *C09C 1/0015* (2013.01); *C09C 1/0018* (2013.01); *C09C 1/0024* (2013.01); *C09C 1/0039* (2013.01); *C09C 1/0051* (2013.01); *C09C 1/0063* (2013.01); *C09C 1/0066* (2013.01); *C09D 5/36* (2013.01); *C09D 11/037* (2013.01); *A61K 2800/412* (2013.01); *A61K 2800/43* (2013.01); *A61K 2800/436* (2013.01); *C01P 2004/51* (2013.01); *C01P 2004/61* (2013.01); *C01P 2006/62* (2013.01); *C01P 2006/63* (2013.01); *C01P 2006/64* (2013.01); *C01P 2006/65* (2013.01); *C09C 2200/102* (2013.01); *C09C 2200/1025* (2013.01); *C09C 2200/1033* (2013.01); *C09C 2200/24* (2013.01); *C09C 2200/301* (2013.01); *C09C 2200/302* (2013.01); *C09C 2200/303* (2013.01); *C09C 2200/304* (2013.01); *C09C 2200/306* (2013.01)

(56) References Cited

U.S. PATENT DOCUMENTS

| | | | |
|---|---|---|---|
| 7,396,401 B2 | 7/2008 | Jungnitz | |
| 7,485,183 B2 | 2/2009 | Hochstein | |
| 7,604,862 B2 | 10/2009 | Ambrosius | |
| 7,691,196 B2 | 4/2010 | Pfaff et al. | |
| 7,891,293 B2 | 2/2011 | Becker | |
| 8,007,583 B2 | 8/2011 | Fuller et al. | |
| 8,016,909 B2 | 9/2011 | Wheeler | |
| 8,129,021 B2 | 3/2012 | Kaupp | |
| 8,337,611 B2 | 12/2012 | Pfaff et al. | |
| 8,500,901 B2 | 8/2013 | Rueger | |
| 2004/0123779 A1 | 7/2004 | Bagala et al. | |
| 2004/0139889 A1 | 7/2004 | Zimmermann et al. | |
| 2005/0019575 A1* | 1/2005 | Jungnitz | C09C 1/0018 428/403 |
| 2005/0147724 A1 | 7/2005 | Schweinfurth | |
| 2005/0166799 A1 | 8/2005 | Fuller et al. | |
| 2008/0047470 A1 | 2/2008 | Pfaff et al. | |
| 2008/0134940 A1 | 6/2008 | Wheeler | |
| 2009/0220557 A1* | 9/2009 | Pfaff | A61K 8/11 252/588 |
| 2010/0064938 A1* | 3/2010 | Voit | C09C 1/64 524/441 |
| 2010/0151047 A1 | 6/2010 | Pfaff et al. | |
| 2010/0196296 A1 | 8/2010 | Geissler | |
| 2010/0298469 A1* | 11/2010 | Kaupp | C09D 7/67 977/773 |
| 2011/0297887 A1 | 12/2011 | Wheeler | |
| 2013/0164356 A1 | 6/2013 | Pfaff | |

FOREIGN PATENT DOCUMENTS

| | | |
|---|---|---|
| CN | 101137723 A | 3/2008 |
| CN | 101282804 A | 10/2008 |
| DE | 10329780 A1 | 10/2004 |
| DE | 102004032799 A1 | 2/2005 |
| DE | 102007041027 A1 | 3/2009 |
| JP | 2003-055575 A | 2/2003 |
| JP | 2004-292816 A | 10/2004 |
| JP | 2005-502738 A | 1/2005 |
| JP | 2005515769 A | 6/2005 |
| JP | 2006-510797 A | 3/2006 |
| JP | 2006-341592 A | 12/2006 |
| WO | 2006082415 A2 | 8/2006 |
| WO | 2007020364 A | 2/2007 |

OTHER PUBLICATIONS

Sven Lohmander. "Influence of shape and a shape factor of pigment particles on the packing ability in coating layers." Nordic Pulp and Paper Rsearch Journal, vol. 15, No. 4, 2000, pp. 300-305. (Year: 2000).*
"Phoenix Colour Card: Pearlescent Pigments", Eckart, 2001, XP003035447 (Wtih English translation Column on Left) Color charts for Phoenix Silver Pearls, Interference Colours and Earth Tone Colours. ( Non-patent iterature filed on Apr. 4, 2014 by a third party in EP2607432).
Pfaff G. et al: "Spezielle Efektpigmente", 2007, Vincentz Network, pp. 46-47, 50-51, XP003035445 ( Non-patent literature filed on Apr. 4, 2014 by a third party in EP2607432).
Maisch R. and Weigand M.: "Perlglanzpigmente—Physikalische Grundlagen, Eigennschaften, Anwendungen", 1991, Verlag Moderne Industrie, pp. 30-33, XP003035446 (Engish translation of relevant parts thereof and enlargement of table 23) ( Non-patent literature filed on Apr. 4, 2014 by a third party in EP2607432).
Photomicrographs of the Pearlescent pigment Phoenix PX 1001 in 25 fold magnification and 50 fold magnification ( Non-patent literature filed on Apr. 4, 2014 by a third party in EP2607432).
S.F. Santos et al. Method for grinding and delaminating muscovite Mining Science and Technology (China) 21, 7-10, 2011.
English Translation of Notice of Preliminary Rejection (2nd)in corresponding KR application 2012-0149205 dispatched Jun. 10, 2019. (pp. 1-8).
Examination Report in corresponding IN application1439/KOL/ 2012 dispatched Feb. 26, 2019. (pp. 1-6).
Opposition filed in corresponding Japan patent 6027431 dispatched Jul. 25, 2017.
G Pfaff, P Reynders. "Angle-Dependent Optical Effects Deriving from Submicron Structures of Films and Pigments." Chemical Reviews, vol. 99, 1999, pp. 1963-1981.
Taiwan Office Action for TW101148112; dated Feb. 17, 2016.

\* cited by examiner

EFFECT PIGMENTS

SUMMARY OF INVENTION

The present invention relates to effect pigments which are based on flake-form substrates having a circular form factor of 1.2-2 and are coated with at least one high-refractive-index layer, and to the use thereof, inter alia in paints, coatings, printing inks, plastics, and in cosmetic formulations.

Effect pigments, such as, for example, pearlescent pigments or metal-effect pigments, are employed in many areas of industry, in particular in the area of automotive paints, industrial coatings, decorative coatings, in plastics, in paints, printing inks and in cosmetic formulations. Pigments of this type are based on flake-form oblong substrates with a single or multiple coating.

The size of the base substrates is generally not crucial per se in the case of effect pigments and can be matched to the particular application. In general, the flake-form and oblong substrates have a thickness between 0.1 and 5 µm, in particular between 0.2 and 4.5 µm. The size in the two other dimensions is usually between 1 and 250 µm, preferably between 2 and 200 µm and in particular between 5 and 60 µm. The effect pigments offered on the market are generally distinguished by a broad particle-size and thickness distribution.

The optical properties of the effect pigments, such as, for example, color and color flop (i.e. also the angle-dependent change in hue angle, saturation and brightness), are determined to a crucial extent by the refractive indices of the interference layers on the substrate flakes and the geometrical thickness thereof. However, effect pigments generally have the disadvantage that they have an inadequate hiding power and inadequate color saturation.

An object of the present invention is to find effect pigments which have high color saturation and at the same time exhibit a high hiding power without losing their optical properties, in particular the luster and color purity, and are distinguished by advantageous applicational properties. Surprisingly, it has now been found that effect pigments based on flake-form substrates which have a roundish shape have increased color saturation and an increased hiding power compared with effect pigments from the prior art based on substrates having an oblong shape with greater edge roughness.

The present invention therefore relates to effect pigments which are based on flake-form substrates, where the substrates have a circular form factor (circumference$^2$/area standardized to a circle) of 1.2-2, and are coated with at least one high-refractive-index layer having a refractive index of n≥1.8.

Circular form factor in this application is defined as the ratio of the circumference squared to the area standardized to a circle, i.e., the area of the individual particle imaged in transmitted light in a light microscope with 30× magnification. For simplification, the result is divided by 4$\pi$, which then gives 1 for the circular form factor of the ideal circle. The evaluated particles lie substantially flat in the imaging plane, and the number of evaluated particles is sufficiently statistically relevant (N=2000) for the circular form factor average.

The invention furthermore relates to the use of the pigments according to the invention in paints, automotive paints, industrial coatings, coatings, printing inks, plastics, button pastes, ceramic materials, glasses, for coloring seed, as absorber in the laser marking of plastics, glasses, cardboard and paper, as absorbers in the laser welding of plastics, as additives for the coloring of food and pharmaceutical products, as additive for the coloring of coatings of food and pharmaceutical products, in cosmetic formulations, for the preparation of pigment compositions and dry preparations and in anti-counterfeiting elements in documents of value.

Suitable base substrates for the effect pigments according to the invention are transparent flake-form substrates. Preferred substrates are phyllosilicates, such as, for example, natural or synthetic mica, talc, kaolin, graphite, flake-form iron oxides, glass flakes, $SiO_2$ flakes, $Al_2O_3$ flakes, $TiO_2$ flakes or synthetic ceramic flakes, synthetic support-free flakes, LCPs (liquid crystal polymers) or other comparable materials. Very particularly preferred substrate flakes are natural or synthetic mica flakes, glass flakes, $Al_2O_3$ flakes and $SiO_2$ flakes.

For the effect pigments according to the invention, substrate flakes having a circular form factor of 1.2-2, preferably 1.2-1.8, and very particularly preferably 1.2-1.7, are employed.

Preferred substrate flakes have a particle size of 5-60 µm, in particular 5-40 µm. The thickness of the preferred substrate flakes is preferably 0.2-0.6 µm.

In the present patent application, the particle sizes can be determined with the aid of a Malvern UK Mastersizer 2000.

The substrate flakes can be produced, for example, as follows:

Using known mechanical comminution methods, substrate lumps are comminuted and delaminated, for example by grinding, and classified in accordance with the requirements in relation to equivalence diameters and thicknesses of the flakes by means of sedimentation, decantation, air separation and/or sieving.

All mills and stirrers known to the person skilled in the art are used for the grinding process, in particular all high-speed stirrers, dispersers or rotor-stator mills.

The substrate flakes, for example mica or glass flakes, are produced by grinding relatively large lumps or coarse flakes. The substrate flakes formed, generally having a diameter of 50-200 µm, are subsequently introduced into a comminution machine, for example a rotor-stator mill, and water and/or an organic solvent, preferably water, is added. The suspension formed in this way is treated mechanically for several hours in the comminution machine, during which the surface of the flakes is polished smooth. The mechanical loading of the particles during this step is selected so that a permanent shear results in further gentle delamination of particles and in smoothing of the edges and surfaces. A narrow particle-size distribution is achieved by a subsequent classification step in the form of a plurality of, at least ≥2, preferably ≥3, sedimentation steps. The thin and roundish flakes produced in this way have a particle-size distribution of 5-60 µm, a thickness distribution of 0.2-0.6 µm and smooth-polished surfaces having only few sharp edges. The circular form factor is 1.2-2.

During the grinding and classification, relatively small, relatively thick particles and relatively large, relatively thin particles are removed, i.e. large particles tend to be only comminuted, while relatively small particles are delaminated and/or removed by classification.

The additional mechanical treatment and the associated polishing effect produce smoothing of the surface of the substrate particles, with, in addition, the oblong flake shape being converted into a roundish flake shape. The decrease in the circular form factor and the oblong nature is associated with the edges of the substrates becoming smoother and the substrates adopting a rounder shape.

Synthetically produced substrates which are intended to serve as base substrate for effect pigments and are not in the form of coarse lumps or flakes, such as, for example, $Al_2O_3$, $SiO_2$, $Fe_2O_3$, $TiO_2$ or glass are fed directly to the comminution machine, for example a rotor-stator mill, for comminution and polishing of the surface. The circular form factor produced is also 1.2-2.

BRIEF DESCRIPTION OF THE DRAWINGS

Photomicrographs FIGS. 1 and 2 image detail measure 43×35 µm and show that the roundish substrate flakes (FIG. 1) have significantly lower edge roughness compared with the oblong substrate flakes (FIG. 2).

Figure 1:
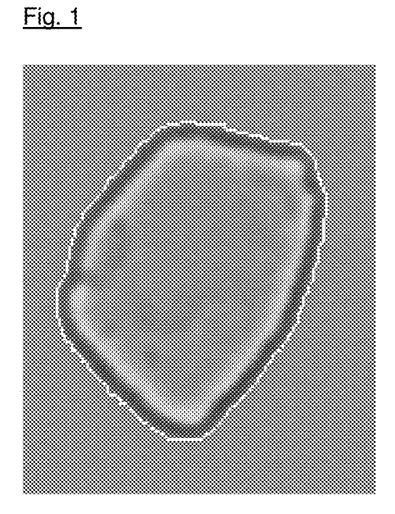
Figure 2:
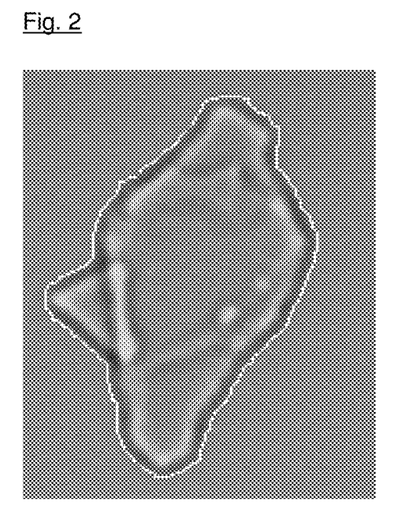

The lower edge roughness and the reduction in the steps on the flake surfaces in general result in very uniform coatings being obtained on coating of the substrate flakes. This relates on the one hand to the local homogeneity of the interference color and also the reduction of scattered-light influences, producing overall higher color saturation, compared with the effect pigments from the prior art.

The roundish substrate flakes can serve as filler, in particular as cosmetic filler, or as base substrate for the production of effect pigments. In this case, the roundish substrate flakes are provided with one or more coatings, preferably metal oxide layers.

The roundish substrate flakes are preferably coated with at least one high-refractive-index layer (n≥1.8).

In the case of substrate flakes which are sensitive to acids and/or bases, such as, for example, glass flakes, it is frequently advisable firstly to coat them with a thin protective layer before the actual coating in order, for example, to prevent leaching-out and/or swelling of the substrates during the coating. However, the protective layer can also serve to achieve an even smoother substrate surface. This protective layer is generally very thin, preferably <20 nm, and thus only has an extremely small influence on the optical properties of the final effect pigment, or none at all. The protective layer is preferably an $SiO_2$ layer.

In this patent application, high-refractive-index is taken to mean a refractive index of n≥1.8, preferably n≥2.0. In this patent application, low-refractive-index is taken to mean a refractive index of n<1.8.

Suitable layer materials are all high-refractive-index materials known to the person skilled in the art which can be applied in a film-like manner and durably to the substrate particles, such as, for example, metal oxides, metal oxide mixtures, metal oxyhydrates, metal sulfides, iron titanates, iron oxide hydrates, titanium suboxides, metals, and mixtures or mixed phases of the said compounds. Particularly suitable are metal oxides or metal oxide mixtures, such as, for example, $TiO_2$, $BiOCl$, $Ce_2O_3$, $Cr_2O_3$, $CoO$, $CO_3O_4$, $Fe_2O_3$, $Fe_3O_4$, $FeOOH$, $NiO$, $SnO_2$, $VO_2$, $V_2O_3$, $ZrO_2$, $ZnO$, $CoAl_2O_4$, $BiVO_4$, iron titanates, iron oxide hydrates, titanium suboxides (partially reduced $TiO_2$ with oxidation numbers from <4 to 2, such as $Ti_3O_5$, $Ti_2O_3$ to $TiO$), and metal sulfides, such as, for example, $Ce_2S_3$, $MoS_2$ and mixtures or mixed phases of the said compounds with one another or with other metal oxides and metals, such as, for example, aluminium, chromium, nickel, silver, gold, titanium, copper or alloys thereof.

If the substrate flakes are coated with one, two or more high-refractive-index layers directly on the surface of the substrate, the coating is preferably a layer of $TiO_2$, $Fe_2O_3$ or a mixture of $TiO_2/Fe_2O_3$ or a $TiO_2$ coating followed by an $Fe_2O_3$ layer.

Multilayered pigments having at least three layers preferably have an alternating coating of high- and low-refractive-index layers. Particular preference is given to a three-layer system on the substrate flake with a high-refractive-index-low-refractive-index-high-refractive-index coating, such as, for example, a $TiO_2$—$SiO_2$—$TiO_2$ coating, where $TiO_2$ is preferably coated directly on the substrate as a first layer.

The thickness of the high-refractive-index layer is generally 20-500 nm, preferably 30-400 nm and in particular 40-350 nm.

Colorless, low-refractive-index materials which are suitable for the coating are preferably metal oxides or the corresponding oxide hydrates, such as, for example, $SiO_2$, $Al_2O_3$, $AlO(OH)$, $B_2O_3$, furthermore $MgF_2$, $MgSiO_3$ or a mixture of the said compounds. The low-refractive-index layer preferably is $SiO_2$, $Al_2O_3$ or $MgF_2$, in particular $SiO_2$.

The thickness of the low-refractive-index layer is preferably 10-200 nm, in particular 10-80 nm and very particularly preferably 20-80 nm.

Besides the said high- and low-refractive-index layers, the effect pigments may additionally be coated with an absorbent layer as the final layer. The effect pigments are then preferably coated with Berlin Blue, Carmine Red, thioindigo or chromium oxide.

The absorbent layer preferably has layer thicknesses of 3-300 nm.

For the preparation of silver-white effect pigments, as described, for example, in EP 1865032 A2, it is advizable to coat the substrate flakes with a high-refractive-index layer which, besides titanium dioxide, comprises at least one low-solubility alkaline-earth metal compound. The refractive index of this layer is ≥1.9, preferably ≥2.0 and in particular ≥2.1. This high-refractive-index coating may consist of a mixture of $TiO_2$ and a low-solubility alkaline-earth metal compound and/or zinc oxide or of two separate layers. In this case, a thin layer of a low-solubility alkaline-earth metal compound or zinc oxide is applied to the $TiO_2$ layer.

The titanium dioxide in the high-refractive-index coating can be in the rutile or anatase modification, preferably in the form of rutile. Processes for the preparation of rutile are described in the prior art, for example in U.S. Pat. Nos. 5,433,779, 4,038,099, 6,626,989, DE 25 22 572 C2, EP 0 271 767 $B_1$. A thin tin dioxide layer (<10 nm), which serves as additive for obtaining the $TiO_2$ as rutile phase, is preferably applied to the substrate flake, preferably a natural or synthetic mica flake, before the $TiO_2$ precipitation.

Preferred effect pigments according to the invention have the following coating directly on the surface of the substrate flake:

substrate flake+$TiO_2$ (anatase)
substrate flake+$SnO_2$+$TiO_2$ (rutile)
substrate flake+$TiO_2$+alkaline-earth metal titanate
substrate flake+$SnO_2$+$TiO_2$+alkaline-earth metal titanate
substrate flake+$TiO_2$+$Fe_2O_3$
substrate flake+$SnO_2$+$TiO_2$+$Fe_2O_3$
substrate flake+$TiO_2$+$Fe_3O_4$
substrate flake+$SnO_2$+$TiO_2$+$Fe_3O_4$
substrate flake+$TiO_2$+$Cr_2O_3$
substrate flake+$SnO_2$+$TiO_2$+$Cr_2O_3$
substrate flake+$TiO_2$+Carmine Red
substrate flake+$SnO_2$+$TiO_2$+Carmine Red
substrate flake+$TiO_2$+Berlin Blue
substrate flake+$SnO_2$+$TiO_2$+Berlin Blue
substrate flake+$TiO_2$/$Fe_2O_3$
substrate flake+$SnO_2$+$TiO_2$/$Fe_2O_3$
substrate flake+$TiO_2$+$SiO_2$+$TiO_2$ substrate flake+$SnO_2$+$TiO_2$+$SiO_2$+$SnO_2$+$TiO_2$
substrate flake+$Fe_2O_3$
substrate flake+$Fe_3O_4$
substrate flake+$TiO_2$+$SiO_2$+$TiO_2$/$Fe_2O_3$
substrate flake+$SnO_2$+$TiO_2$+$SiO_2$+$TiO_2$/$Fe_2O_3$
substrate flake+$TiO_2$+$SiO_2$+$TiO_2$+$TiO_2$/$Fe_2O_3$
substrate flake+$SnO_2$+$TiO_2$+$SiO_2$+$TiO_2$+$TiO_2$/$Fe_2O_3$
substrate flake+$SnO_2$+$TiO_2$+$SiO_2$+$SnO_2$+$TiO_2$+$TiO_2$/$Fe_2O_3$
substrate flake+$TiO_2$/$Fe_2O_3$+$SiO_2$+$TiO_2$+$TiO_2$/$Fe_2O_3$
substrate flake+$TiO_2$/$Fe_2O_3$+$SiO_2$+$SnO_2$+$TiO_2$+$TiO_2$/$Fe_2O_3$
substrate flake+$TiO_2$/$Fe_2O_3$+$SiO_2$+$TiO_2$
substrate flake+$TiO_2$/$Fe_2O_3$+$SiO_2$+$SnO_2$+$TiO_2$
substrate flake+$TiO_2$/$Fe_2O_3$+$SiO_2$+$TiO_2$/$Fe_2O_3$
substrate flake+$TiO_2$+$SiO_2$+$Fe_3O_4$
substrate flake+$TiO_2$+$SiO_2$+$Cr_2O_3$
substrate flake+$Cr_2O_3$
substrate flake+Ag
substrate flake+Au
substrate flake+$Fe_2O_3$+$SiO_2$+$TiO_2$/$Fe_2O_3$
substrate flake+$SiO_2$+$TiO_2$ (anatase)
substrate flake+$SiO_2$+$SnO_2$+$TiO_2$ (rutile)
substrate flake+$SiO_2$+$TiO_2$+alkaline-earth metal titanate
substrate flake+$SiO_2$+$SnO_2$+$TiO_2$+alkaline-earth metal titanate
substrate flake+$SiO_2$+$TiO_2$+$Fe_2O_3$
substrate flake+$SiO_2$+$SnO_2$+$TiO_2$+$Fe_2O_3$
substrate flake+$SiO_2$+$TiO_2$+$Fe_3O_4$
substrate flake+$SiO_2$+$SnO_2$+$TiO_2$+$Fe_3O_4$
substrate flake+$SiO_2$+$TiO_2$+$Cr_2O_3$
substrate flake+$SiO_2$+$SnO_2$+$TiO_2$+$Cr_2O_3$
substrate flake+$SiO_2$+$TiO_2$+Carmine Red
substrate flake+$SiO_2$+$SnO_2$+$TiO_2$+Carmine Red
substrate flake+$SiO_2$+$TiO_2$+Berlin Blue
substrate flake+$SiO_2$+$SnO_2$+$TiO_2$+Berlin Blue
substrate flake+$SiO_2$+$TiO_2$/$Fe_2O_3$
substrate flake+$SiO_2$+$SnO_2$+$TiO_2$/$Fe_2O_3$
substrate flake+$SiO_2$+$TiO_2$+$SiO_2$+$TiO_2$
substrate flake+$SiO_2$+$SnO_2$+$TiO_2$+$SiO_2$+$SnO_2$+$TiO_2$
substrate flake+$SiO_2$+$Fe_2O_3$
substrate flake+$SiO_2$+$Fe_3O_4$
substrate flake+$SiO_2$+$TiO_2$+$SiO_2$+$TiO_2$/$Fe_2O_3$
substrate flake+$SiO_2$+$SnO_2$+$TiO_2$+$SiO_2$+$TiO_2$/$Fe_2O_3$
substrate flake+$SiO_2$+$TiO_2$+$SiO_2$+$TiO_2$+$TiO_2$/$Fe_2O_3$
substrate flake+$SiO_2$+$SnO_2$+$TiO_2$+$SiO_2$+$TiO_2$+$TiO_2$/$Fe_2O_3$
substrate flake+$SiO_2$+$SnO_2$+$TiO_2$+$SiO_2$+$SnO_2$+$TiO_2$+$TiO_2$/$Fe_2O_3$
substrate flake+$SiO_2$+$TiO_2$/$Fe_2O_3$+$SiO_2$+$TiO_2$+$TiO_2$/$Fe_2O_3$
substrate flake+$SiO_2$+$TiO_2$/$Fe_2O_3$+$SiO_2$+$SnO_2$+$TiO_2$+$TiO_2$/$Fe_2O_3$
substrate flake+$SiO_2$+$TiO_2$/$Fe_2O_3$+$SiO_2$+$TiO_2$
substrate flake+$SiO_2$+$TiO_2$/$Fe_2O_3$+$SiO_2$+$SnO_2$+$TiO_2$
substrate flake+$SiO_2$+$TiO_2$/$Fe_2O_3$+$SiO_2$+$TiO_2$/$Fe_2O_3$
substrate flake+$SiO_2$+$TiO_2$+$SiO_2$+$TiO_2$/$Fe_2O_3$
substrate flake+$SiO_2$+$TiO_2$+$SiO_2$+$Fe_3O_4$
substrate flake+$SiO_2$+$TiO_2$+$SiO_2$+$Cr_2O_3$
substrate flake+$SiO_2$+$Cr_2O_3$
substrate flake+$SiO_2$+Ag
substrate flake+$SiO_2$+Au
substrate flake+$SiO_2$+$Fe_2O_3$+$SiO_2$+$TiO_2$/$Fe_2O_3$
substrate flake+$TiO_2$ (anatase)+$SiO_2$
substrate flake+$SnO_2$+$TiO_2$ (rutile)+$SiO_2$.

The coating of the roundish substrate flakes having a circular form factor of 1.2-2 is preferably carried out by wet-chemical methods. To this end, the wet-chemical coating methods developed for the preparation of pearlescent pigments are preferably used. Methods of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or also in further patent documents and other publications known to the person skilled in the art.

The effect pigments according to the invention are generally prepared by suspending the roundish substrate flakes in water and adding one or more hydrolysable metal salts at a pH which is suitable for precipitation and which is selected in such a way that the metal oxide or metal oxide hydrate is deposited directly onto the flakes without significant secondary precipitations occurring. The pH is usually kept constant by simultaneous metered addition of a base or acid. After filtration and washing, the coated substrates are firstly dried for 20-60 min at temperatures of 50-150° C., preferably 80-120° C., and subsequently calcined at 600 to 1200° C., preferably at 700-1000° C., in particular at 700-900° C., for 0.3-1 h, preferably 0.5-0.8 h.

The coating, for example with a $TiO_2$ layer, can furthermore also be carried out in a fluidized-bed reactor by gas-phase coating, it being possible to use correspondingly, for example, the methods proposed in EP 0 045 851 A1 and EP 0 106 235 A1 for the preparation of pearlescent pigments.

The coating of the substrate flakes with titanium dioxide is preferably carried out by a wet-chemical method by the chloride or sulfate process.

In order additionally to increase the light, water and weather stability, it is frequently advisable to subject the finished effect pigment to post-coating or post-treatment, depending on the area of application. Suitable post-coatings or post-treatments are, for example, the processes described in German Patent 22 15 191, DE-A 31 51 354, DE-A 32 35 017 or DE-A 33 34 598. This post-coating further increases the chemical stability or simplifies handling of the pigment, in particular incorporation into various media. In order to improve the wettability, dispersibility and/or compatibility with the user media, it is possible to apply functional coatings comprising $Al_2O_3$ or $ZrO_2$ or mixtures or mixed phases thereof to the pigment surface. Furthermore, organic or combined organic/inorganic post-coatings are possible, for example with silanes, as described, for example, in EP 0090259, EP 0 634 459, WO 99/57204, WO 96/32446, WO 99/57204, U.S. Pat. Nos. 5,759,255, 5,571,851, WO 01/92425, WO 2006/021386 A1 or in J. J. Ponjeé, Philips Technical Review, Vol. 44, No. 3, 81 ff. and P. H. Harding, J. C. Berg, J. Adhesion Sci. Technol. Vol. 11, No. 4, pp. 471-493.

The outer, optional protective layer is preferably one or two metal-oxide layers of the elements Si, Al or Ce. Particular preference is given here to a layer sequence in which firstly a cerium oxide layer has been applied, which is then followed by an $SiO_2$ layer, as described, for example, in WO 2006/021386 A1.

The outer protective layer may furthermore be organo-chemically modified on the surface. For example, one or more silanes may be applied to this outer protective layer. The silanes may be alkylsilanes having branched or unbranched alkyl radicals having 1 to 24 C atoms, preferably 6 to 18 C atoms.

However, the silanes may also be organofunctional silanes which facilitate chemical bonding to a plastic, a binder of a surface coating or an ink, etc.

The organofunctional silanes containing suitable functional groups which are preferably used as surface modifiers are commercially available and are produced, for example, by Degussa, Rheinfelden, Germany, and marketed under the trade name "Dynasylan®". Further products can be purchased from OSi Specialties (Silquest® silanes) or from Wacker, for example standard and α-silanes from the GENIOSIL® product group.

Examples thereof are 3-methacryloxypropyltrimethoxysilane (Dynasylan MEMO, Silquest A-174NT), vinyltri(m)ethoxysilane (Dynasylan VTMO or VTEO, Silquest A-151 or A-171), 3-mercaptopropyltri(m)ethoxysilane (Dynasylan MTMO or 3201; Silquest A-189), 3-glycidoxypropyltrimethoxysilane (Dynasylan GLYMO, Silquest A-187), tris-(3-trimethoxysilylpropyl) isocyanurate (Silquest Y-11597), gammamercaptopropyltrimethoxysilane (Silquest A-189), bis-(3-triethoxysilylpropyl) polysulfide (Silquest A-1289), bis-(3-triethoxysilyl) disulfide (Silquest A-1589), beta-(3,4-epoxycyclohexyl)ethyltrimethoxysilane (Silquest A-186), bis(triethoxysilyl)ethane (Silquest Y-9805), gammaisocyanatopropyltrimethoxysilane (Silquest A-Link 35, GENIOSIL GF40), (methacryloxymethyl)tri(m)ethoxysilane (GENIOSIL XL 33, XL 36), (methacryloxymethyl)(m)ethyldimethoxysilane (GENIOSIL XL 32, XL 34), (isocyanatomethyl)trimethoxysilane (GENIOSIL XL 43), (isocyanatomethyl)methyldimethoxysilane (GENIOSIL XL 42), (isocyanatomethyl)trimethoxysilane (GENIOSIL XL 43), 3-(triethoxysilyl)propylsuccinic anhydride (GENIOSIL GF 20), (methacryloxymethyl)methyldiethoxysilane, 2-acryloxyethylmethyldimethoxysilane, 2-methacryloxyethyltrimethoxysi lane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-methacryloxypropyltriethoxysilane, 3-methacryloxypropyltriacetoxysilane, 3-methacryloxypropylmethyldimethoxysilane, vinyltrichlorosilane, vinyltrimethoxysilane (GENIOSIL XL 10), vinyltris(2-methoxyethoxy)silane (GENIOSIL GF 58), vinyltriacetoxysilane.

However, it is also possible to use other organofunctional silanes on the effect pigments according to the invention.

Furthermore, it is possible to employ aqueous pre-hydrolyzates, commercially available, for example, from Degussa. These include, inter alia, aqueous, alcohol-free aminosilane hydrolyzate (Dynasylan Hydrosil 1151), aqueous, alcohol-free amino/alkyl-functional siloxane co-oligomer (Dynasylan Hydrosil 2627), aqueous, alcohol-free diamino/alkyl-functional siloxane co-oligomer (Dynasylan Hydrosil 2776), aqueous, alcohol-free amino/vinyl-functional siloxane co-oligomer (Dynasylan Hydrosil 2907), aqueous, alcohol-free amino/alkyl-functional siloxane co-oligomer (Dynasylan Hydrosil 2909), aqueous, alcohol-free epoxy-functional siloxane oligomer (Dynasylan Hydrosil 2926) or aqueous, alcohol-free amino/methacrylate-functional siloxane co-oligomer (Dynasylan Hydrosil 2929), oligomeric diaminosilane system (Dynasylan 1146), vinyl/alkyl-functional siloxane co-oligomer (Dynasylan 6598), vinyl- and methoxy group-containing vinylsilane concentrate (oligomeric siloxane) (Dynasylan 6490) or oligomeric short-chain alkyl-functional silane (Dynasylan 9896).

In a preferred embodiment, the organofunctional silane mixture comprises at least one amino-functional silane besides at least one silane containing no functional bonding group. The amino function is a functional group which is able to undergo one or more chemical interactions with the groups usually present in binders. This may include a covalent bond, such as, for example, with isocyanate or carboxylate functions of the binder, or hydrogen bonds, such as with OH or COOR functions, or also ionic interactions. An amino function is therefore very highly suitable for the purpose of chemical bonding of the effect pigment to binders of different types.

The following compounds are preferably used for this purpose:

aminopropyltrimethoxysilane (Dynasylan AMMO; Silquest A-1110), aminopropyltriethoxysilane (Dynasylan AMEO) or N-(2-aminoethyl)-3-aminopropyltrimethoxysilane (Dynasylan DAMO, Silquest A-1120) or N-(2-aminoethyl)-3-aminopropyltriethoxysilane, triamino-functional trimethoxysilane (Silquest A-1130), bis(gamma-trimethoxysilylpropyl)amine (Silquest A-1170), N-ethyl-gamma-aminoisobutyltrimethoxysilane (Silquest A-Link 15), N-phenyl-gamma-aminopropyltrimethoxysilane (Silquest Y-9669), 4-amino-3,3-dimethylbutyltrimethoxysilane (Silquest Y-11637), N-cyclohexylaminomethylmethyldiethoxysilane (GENIOSIL XL 924), (N-cyclohexylaminomethyl)triethoxysilane (GENIOSIL XL 926), (N-phenylaminomethyl)trimethoxysilane (GENIOSIL XL 973) or mixtures thereof.

In a furthermore preferred embodiment, the silane containing no functional bonding group is an alkylsilane. The alkylsilane preferably has the formula z here is an integer from 1 to 3, R is a substituted or unsubstituted, unbranched or branched alkyl chain having 10 to 22 C atoms, and X stands for a halogen and/or alkoxy group. Preference is given to alkylsilanes having alkyl chains having at least 12 C atoms. R may also be cyclically bonded to Si, where in this case z is usually 2.

A silane of this type effects stronger hydrophobicisation of the pigment surface. This in turn results in the effect pigment coated in this way tending to float upwards in the surface coating. In the case of flake-form effect pigments, this type of behavior is known as "leafing" behavior.

A silane mixture consisting of at least one silane which contains at least one functional group which facilitates bonding to the binder, and an alkylsilane containing no amino group which is insoluble or sparingly soluble in water facilitates optimum applicational properties of the effect pigments. An organochemical surface modification of this type results in the effect pigments aligning extremely well in a surface-coating or paint layer, i.e. essentially plane-parallel to the coated or painted substrate, and at the same time reacting chemically with the binder system of the surface coating or paint and consequently being covalently bonded in the surface-coating or paint layer. Surface-coating or paint layers of this type have increased mechanical and chemical resistance to environmental influences, such as, for example, weather, etc.

Besides the high color saturation and a very bright and high luster, the effect pigments according to the invention are distinguished by a very high hiding power and low edge roughness. The pigments are therefore also very highly suitable, owing to their good skin feeling, for cosmetic formulations.

Since the effect pigments according to the invention, besides high hiding power, have a bright and strong luster with high color saturation, particularly effective effects in the various application media can be achieved with them.

It goes without saying that, for the various applications, the effect pigments according to the invention may also advantageously be used as a mixture with organic dyes, organic pigments or inorganic pigments, such as, for example, transparent and opaque white, colored and black pigments, and also with flake-form iron oxides, holographic pigments, LCPs (liquid crystal polymers) or with pearlescent pigments, etc. No limits are set for the mixing ratios and concentrations.

The effect pigments according to the invention can be mixed with commercially available pigments and fillers in any ratio by weight. The ratio can be 1:1 to 9:1 is preferred. If the effect pigments according to the invention are mixed with fillers, the mixing ratio can also be 99:1 to 1:99.

The effect pigments according to the invention are compatible with a multiplicity of color systems, preferably from the area of paints, coatings and printing inks. For the preparation of printing inks for, for example, gravure printing, flexographic printing, offset printing, offset overprint varnishing, a multiplicity of binders, in particular water-soluble grades, is suitable, as marketed, for example, by the BASF, Marabu, Pröll, Sericol, Hartmann, Gebr. Schmidt, Sicpa, Aarberg, Siegberg, GSB-Wahl, Follmann, Ruco or Coates Screen INKS GmbH companies. The printing inks can be water-based or solvent-based. Furthermore, the effect pigments according to the invention are also suitable for the laser marking of paper and plastics, and for applications in the agricultural sector, for example for greenhouse sheeting, and, for example, for coloring tarpaulins.

The effect pigments according to the invention can be used for pigmenting surface coatings, printing inks, plastics, agricultural sheeting, seed coatings, food colorings, button pastes, medicament coatings or cosmetic formulations, such as lipsticks, nail varnishes, compact powders, shampoos, soaps, loose powders and gels. The concentration of the pigment in the application system to be pigmented is generally between 0.1 and 70% by weight, preferably between 0.1 and 50% by weight and in particular between 0.5 and 10% by weight, based on the total solids content of the system. It is generally dependent on the specific application.

In plastics comprising the effect pigments according to the invention, preferably in amounts of 0.01 to 50% by weight, in particular 0.1 to 7% by weight, particularly pronounced color effects can be achieved.

In the surface coatings sector, in particular in automobile paints, the effect pigments are employed in amounts of 0.1-20% by weight, preferably 1 to 10% by weight, including for 3-coat systems.

In surface coatings, the effect pigments according to the invention have the advantage that the target gloss is achieved by a single-layer finish (one-coat system or base coat in a two-coat system). Compared with finishes which comprise, for example, a multilayered pigment based on mica or a conventional pearlescent pigment based on a substrate having a broad thickness distribution instead of the effect pigments according to the invention, finishes comprising the pigments according to the invention exhibit a clearer depth effect and a more pronounced color and gloss effect.

The effect pigments according to the invention can also advantageously be employed in decorative and care cosmetics. The use concentration extends from 0.01% by weight in shampoo to 100% by weight in the case of loose powders. In the case of a mixture of the pigments according to the invention with fillers, preferably with spherical fillers, such as, for example, $SiO_2$, the concentration in the formulation can be 0.01-70% by weight. The cosmetic products, such as, for example, nail varnishes, compact powders, shampoos, loose powders and gels, are distinguished by particularly interesting color effects and high luster.

Furthermore, the effect pigments according to the invention can be employed in bath additives, toothpastes and for the finishing of foods, for example mass coloring and/or coatings of boiled sweets, wine gums, such as, for example, jelly babies, pralines, licorice, confectionery, sticks of rock, blancmange, fizzy drinks, sodas, etc., or as a coating, for example, in dragees and tablets in the pharmaceuticals sector.

The effect pigments according to the invention can furthermore be mixed with commercially available fillers. Fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-form, spherical or needle-shaped as required.

It is of course also possible for the effect pigments according to the invention to be combined in the formulations with cosmetic raw materials and assistants of any type. These include, inter alia, oils, fats, waxes, film formers, preservatives and assistants which generally determine the applicational properties, such as, for example, thickeners and rheological additives, such as, for example, bentonites, hectorites, silicon dioxides, Ca silicates, gelatines, high-molecular-weight carbohydrates and/or surface-active assistants, etc.

The formulations comprising the effect pigments according to the invention can belong to the lipophilic, hydrophilic or hydrophobic type. In the case of heterogeneous formulations having discrete aqueous and nonaqueous phases, the effect pigments according to the invention may in each case be present in only one of the two phases or alternatively distributed over both phases.

The pH values of the formulations can be between 1 and 14, preferably between 2 and 11 and particularly preferably between 5 and 8.

No limits are set for the concentrations of the effect pigments according to the invention in the formulation. They can be—depending on the application—between 0.001 (rinse-off products, for example shower gels) and 100% (for example luster-effect articles for particular applications).

The effect pigments according to the invention may furthermore also be combined with cosmetic active ingredients. Suitable active ingredients are, for example, insect repellents, UV A/BC protection filters (for example OMC, B3 and MBC), anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, ectoin, emblica, allantoin, bioflavonoids and derivatives thereof.

In the pigmenting of binder systems, for example for surface coatings and printing inks for gravure printing, offset printing or screen printing, or as precursors for printing inks, the use of the effect pigments according to the invention in the form of highly pigmented pastes, granules, pellets, etc., has proven particularly suitable. The effect pigments are generally incorporated into the printing ink in amounts of 2-35% by weight, preferably 5-25% by weight and in particular 8-20% by weight. Offset printing inks can comprise the pigments in amounts of up to 40% by weight or more. The precursors for printing inks, for example in the form of granules, as pellets, briquettes, etc., comprise up to 98% by weight of the pigments according to the invention in addition to the binder and additives. Printing inks comprising the pigments according to the invention exhibit purer hues than with conventional effect pigments. The particle thicknesses of the effect pigments according to the invention are relatively small and therefore cause particularly good printability.

The effect pigments according to the invention are furthermore suitable for the preparation of flowable pigment compositions and dry preparations, in particular for printing inks, comprising one or more pigments according to the invention, binders and optionally one or more additives. The present invention furthermore relates to the use of the effect pigments according to the invention in paints, coatings, powder coatings, automotive paints and industrial coatings, printing inks, plastics, button pastes, ceramic materials, glasses, for coating seed, as absorber in the laser marking of plastics, glasses, cardboard and paper, as absorber in the laser welding of plastics, for coloring food and pharmaceutical products, for coloring coatings of food and pharmaceutical products, in cosmetic formulations and in anti-counterfeiting-elements in documents of value, such as, for example, banknotes, credit cards, identity documents, etc. Furthermore, the pigments according to the invention are also suitable for the preparation of pigment compositions and for the preparation of dry preparations, such as, for example, granules, chips, pellets, briquettes, etc. The dry preparations are particularly suitable for printing inks and for cosmetic formulations.

The invention thus also relates to formulations comprising the effect pigments according to the invention.

The invention relates, in particular, to formulations which, besides the effect pigments according to the invention, comprise at least one constituent selected from the group of the absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilizers, dyes, humectants, film formers, fillers, odor substances, flavor substances, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. DE 102011 121 804.5, filed Dec. 21, 2011 and DE 102012 000 887.2, filed Jan. 19, 2012 are incorporated by reference herein.

EXAMPLES

I. Production of the Substrates

Example 1a 1 kg of Muscovite mica, which is in the form of coarse flakes, is ground to a particle size of less than 200 µm by a Koller process. The fine mica flakes formed in this way are introduced into a rotor-stator mill, and 1 l of deionized water is added. The resultant suspension is ground in the mill for 5 hours, during which the surface of the flakes is polished smooth at the same time. The mechanical loading of the particles during the grinding step is selected so that a permanent shear results in further gentle delamination of particles and in smoothing of the edges and surfaces. A narrow particle-size distribution is achieved by a subsequent classification step in the form of a plurality of (at least 3 steps) sedimentation steps. The mica flakes produced in this way have a particle-size distribution of 10-40 µm, a thickness distribution of 0.2 to 0.6 µm (in each case 90% of all particles) and a smooth-polished surface having only few sharp edges. The circular form factor is 1.6.

Example 1b 1 kg of synthetic mica flakes is treated analogously to Example 1a. Synthetic mica flakes having a circular form factor of 1.6 are obtained.

II. Coating of the Substrate Flakes

Example 2.1: Natural Mica+$SnO_2$+$TiO_2$ 100 g of natural mica flakes from Example 1a are warmed to 75° C. in 2 l of deionized water with stirring. The coating pH of 1.8 is established by dropwise addition of an $SnCl_4$ solution (22 g/l). The remainder of 100 ml of $SnCl_4$ solution (22 g/l) is subsequently metered in. During this addition, the pH is kept constant at 1.8 using 32% sodium hydroxide solution. When the addition is complete, the mixture is stirred for a further 10 minutes.

At constant pH, 490 ml of a $TiOCl_2$ solution (400 g of $TiCl_4$/l) are then metered in until the color end point (yellow) has been reached, during which the pH being is constant at 1.8 by simultaneous dropwise addition of 32% sodium hydroxide solution.

When the addition is complete, the mixture is stirred for a further 10 minutes, the suspension is filtered off with suction and washed with deionized water until salt-free. After drying at 120° C. (24 h), the pigment is calcined at 800° C. for 45 minutes.

A high-luster, intensely colored pigment having a yellow interference color is obtained.

Example 2.2: Synthetic Mica+$SnO_2$+$TiO_2$+$SiO_2$+ $SnO_2$+$TiO_2$ 75 g of synthetic mica flakes from Example 1b are warmed to 75° C. with 1500 ml of deionized water with stirring. The pH of the suspension is then adjusted to 1.8 using hydrochloric acid (15% HCl). 75 ml of $SnCl_4$ solution (22 g/l) are subsequently metered in. During this addition, the pH is kept constant at 1.8 using 32% sodium hydroxide solution. When the addition is complete, the mixture is stirred for a further 10 minutes.

A $TiOCl_2$ solution (400 g of $TiCl_4$/l) is subsequently metered in to the color end point (yellow), during which the pH is kept constant at 1.8 by simultaneous dropwise addition of 32% sodium hydroxide solution.

By color measurement during the coating process, the coloristic properties during preparation of the pigment are monitored and the precipitation process is controlled in accordance with the hue (hue angle arc tan b*/a*).

The coating is stopped, and stirring is subsequently continued for 15 minutes.

The pH is subsequently adjusted to pH=9.0 using dilute sodium hydroxide solution. 100 ml of a sodium water-glass solution having a content of 2% are then added, during which the pH is kept constant by means of hydrochloric acid (10% HCl). The mixture is subsequently stirred for a further 30 minutes.

The pH is reduced to 1.8 by dropwise addition of hydrochloric acid (w=20%). 75 ml of $SnCl_4$ solution (22 g/l) are metered in. During this addition, the pH is kept constant at 1.8 using 32% sodium hydroxide solution. When the addition is complete, the mixture is stirred for a further 10 minutes. At constant pH, 300 ml of $TiOCl_2$ solution (400 g of $TiCl_4$/l) are then metered in until the color end point (green) has been reached, during which the pH is kept constant at 1.8 by simultaneous dropwise addition of 32% sodium hydroxide solution.

After a post-stirring time of 15 minutes, the pigment is separated off from the supernatant reaction solution by filtration and washed until salt-free. After drying at 120° C. (24 h), the pigment is calcined at 800° C. for 45 minutes.

A high-luster, intensely colored pigment having a green interference color is obtained.

III. Comparison of the Lab Values of Iriodin® 205 with the Pigment from Example 2.1

The Lab values (measured using an Eta measuring instrument, measurement angle 75°/95° are determined with reference to black/white coating cards (NC lacquer) for Iriodin® 205 (yellow interference pigment on mica flakes) from Merck KGaA and for the pigment from Example 2.1:

|  | Iriodin ® 205 Prior art | Pigment from Example 2.1 Invention |
|---|---|---|
| L value | 119.8 | 126.6 |
| a value | 8.7 | 10.3 |
| b value | 63.0 | 74.6 |
| Chroma $\sqrt{(a^2 + b^2)}$ | 63.6 | 75.3 |

The significantly increased a and b values of the pigment according to the invention mean that a significantly improved chroma is achieved, while the high L value indicates increased luster.

USE EXAMPLES

Example A: Shower Gel

| Phase A | | | |
|---|---|---|---|
| Raw material | Source of supply | INCI | [%] |
| Pigment from Example 2.1 | Merck KGaA | | 0.10 |
| Keltrol T | Kelco | Xanthan Gum | 0.75 |
| Water, demineralized | | Aqua (Water) | 64.95 |

| Phase B | | | |
|---|---|---|---|
| Raw material | Source of supply | INCI | [%] |
| Plantacare 2000 UP | Cognis GmbH | Decyl Glucoside | 20.00 |
| Texapon ASV 50 | Cognis GmbH | Sodium Laureth Sulfate, Sodium Laureth-8 Sulfate, Magnesium Laureth Sulfate, Magnesium Laureth-8 Sulfate, Sodium Oleth Sulfate, Magnesium Oleth Sulfate | 3.60 |
| Bronidox L | Cognis GmbH | Propylene Glycol, 5-Bromo-5-Nitro-1,3-Dioxane | 0.20 |
| Everest 79658 SB perfume oil | Haarmann & Reimer GmbH | Perfume | 0.05 |
| 1% FD&C Blue No. 1 in water | BASF AG | Aqua (Water), CI 42090 (FD&C Blue No. 1) | 0.20 |

| Phase C | | | |
|---|---|---|---|
| Raw material | Source of supply | INCI | [%] |
| Citric acid monohydrate | Merck KGaA/Rona ® | Citric Acid | 0.15 |
| Water, demineralized | | Aqua (Water) | 10.00 |

Preparation:

For phase A, stir the interference pigment into the water. Slowly scatter in the Keltrol T with stirring and stir until it has dissolved. Add phases B and C successively while stirring slowly until everything is homogeneously distributed. Adjust the pH to 6.0 to 6.4.

Example B: Nail Varnish

| Raw material | Source of supply | INCI | [%] |
|---|---|---|---|
| Pigment from Example 2.2 | Merck KGaA | | 2.00 |
| Thixotropic nail varnish base 1348 | International Lacquers S.A. | Toluene, Ethyl Acetate, Butyl Acetate, Nitrocellulose, Tosylamide/Formaldehyde Resin, Dibutyl Phthalate, Isopropyl Alcohol, Stearalkonium Hectorite, Camphor, Acrylates Copolymer, Benzophenone-1 | 98.00 |

Preparation:

The interference pigment is weighed out together with the varnish base, mixed well by hand using a spatula and subsequently stirred at 1000 rpm for 10 min.

Example C: Coating System

90% by weight of Hydroglasur BG/S colorless (water-based coating from. Ernst Diegel GmbH)
10% by weight of pigment from Example 2.2
Coating by spraying-on at 80° C.
    5 min pre-drying at 80° C.
    20 min baking at 180° C.

Example D: Plastic 1 kg of polystyrene granules is wetted uniformly with 5 g of coupling agent in a tumble mixer. 42 g of green interference pigment from Example 2.2 are then added, and the mixture is mixed for 2 min. These granules are converted into stepped plates measuring 4×3×0.5 cm in an injection-moulding machine under conventional conditions. The stepped plates are distinguished by their pronounced sparkle effect.

Example E: Coloring of Confectionery

Raw materials: effervescent candies white
Spray Solution:
    94% of alcoholic shellac solution from Kaul
    6% of effect pigment from Example 2.1
The effervescent candies are sprayed with an interference pigment/shellac solution until the desired color application has been achieved. Subsequent drying using cold air is possible.

Example F: Automotive Paint

The pigment from Example 2.2 can easily be incorporated into automotive paints. To this end, the pigment from Example 2.2 is added to the paint base with stirring. The stirring operation is continued until the pigment has uniformly distributed in the paint. The colored paint is sprayed onto aluminium test sheets coated black and white.
Production of the Painted Sheets:
Paint: Herberts base coat 419982
Pigmentation: 5%
Dry layer thickness: 15 μm
Spray gun: Sprimag S 233; nozzle diameter: 1.5 mm
Spray pressure: 4 bar
Nozzle/substrate separation: 27 cm Example G: Flexographic Printing Preparation of the Printing Ink:
    The pigment from Example 2.1 is pre-wetted with prewetting Byk 348 (0.6%) and incorporated into the binder in a concentration of 22.9%.
Binder: Koustom Kote 9000/USA, Water-Based
    The paste is diluted with water until a viscosity of 40 sec with the 4 mm Erichsen cup at 25° C. has been reached.
    The pigments are printed onto matt-black art paper from an anilox ceramic cylinder (24 ccm/m$^2$) via a rubber printing plate.
    The pigments according to the invention exhibit high color intensity.
    The products from Use Examples A-G are distinguished by their high luster, high color intensity and high color purity.
    The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An effect pigment comprising a roundish flake-form substrate having a circular form factor of circumference$^2$/area standardized to a circle of 1.2-2 coated with at least one high-refractive-index layer having a refractive index of n≥1.8,
    wherein the flake-form substrate is synthetic mica flakes, natural mica flakes, $SiO_2$ flakes, $Al_2O_3$ flakes, glass flakes, iron oxide flakes, graphite flakes, $TiO_2$ flakes or mixtures thereof,
    wherein the high-refractive-index layer comprises at least one metal oxide, metal sulfide, iron titanate, iron oxide hydrate, titanium suboxide, $TiO_2$, BiOCl, $Ce_2O_3$, $Cr_2O_3$, COO, $Co_3O_4$, $Fe_2O_3$, $F_3O_4$, FeOOH, NiO, $SnO_2$, $VO_2$, $V_2O_3$, $ZrO_2$, ZnO, $CoAl_2O_4$, $BiVO_4$, $Ti_3O_5$, $Ti_2O_3$, TiO, $Ce_2S_3$, $MoS_2$, or mixtures or mixed phases of said compounds with one another; and
    wherein the roundish shape results in increased color saturation and hiding power compared with a non-roundish pigment with oblong shape and greater edge roughness.

2. The effect pigment according to claim 1, wherein the substrate has a circular form factor of 1.2-1.8.

3. The effect pigment according to claim 1, wherein the substrate has a particle size of 5-60 μm.

4. The effect pigment according to claim 1, wherein the substrate has a thickness of 0.2-0.6 μm.

5. The effect pigment according to claim 1, wherein the flake-form substrate is a mica or glass flake.

6. The effect pigment according to claim 1, wherein the flake-form substrate is a natural mica flake.

7. The effect pigment according to claim 1, wherein the high-refractive-index layer comprises one or more metal oxides.

8. The effect pigment according to claim 1, wherein the substrate is coated with at least one high-refractive-index layer having a refractive index n≥1.8 and at least one low-refractive-index layer having an n<1.8.

9. The effect pigment according to claim 8, wherein the low-refractive-index layer is $SiO_2$, $Al_2O_3$, AlO(OH), or $MgF_2$.

10. The effect pigment according to claim 1, having the following layer sequence:
    substrate flake+$TiO_2$ (anatase)
    substrate flake+$SnO_2$+$TiO_2$ (rutile)
    substrate flake+$TiO_2$+alkaline-earth metal titanate
    substrate flake+$SnO_2$+$TiO_2$+alkaline-earth metal titanate
    substrate flake+$TiO_2$+$Fe_2O_3$
    substrate flake+$SnO_2$+$TiO_2$+$Fe_2O_3$
    substrate flake+$TiO_2$+$Fe_3O_4$
    substrate flake+$SnO_2$+$TiO_2$+$Fe_3O_4$
    substrate flake+$TiO_2$+$Cr_2O_3$
    substrate flake+$SnO_2$+$TiO_2$+$Cr_2O_3$
    substrate flake+$TiO_2$+Carmine Red
    substrate flake+$SnO_2$+$TiO_2$+Carmine Red
    substrate flake+$TiO_2$+Berlin Blue
    substrate flake+$SnO_2$+$TiO_2$+Berlin Blue
    substrate flake+$TiO_2$/$Fe_2O_3$
    substrate flake+$SnO_2$+$TiO_2$/$Fe_2O_3$
    substrate flake+$TiO_2$+$SiO_2$+$TiO_2$
    substrate flake+$SnO_2$+$TiO_2$+$SiO_2$+$SnO_2$+$TiO_2$
    substrate flake+$Fe_2O_3$
    substrate flake+$Fe_3O_4$
    substrate flake+$TiO_2$+$SiO_2$+$TiO_2$/$Fe_2O_3$ substrate flake+$SnO_2$+$TiO_2$+$SiO_2$+$TiO_2$/$Fe_2O_3$
substrate flake+$TiO_2$+$SiO_2$+$TiO_2$+$TiO_2$/$Fe_2O_3$
substrate flake+$SnO_2$+$TiO_2$+$SiO_2$+$TiO_2$+$TiO_2$/$Fe_2O_3$
substrate flake+$SnO_2$+$TiO_2$+$SiO_2$+$SnO_2$+$TiO_2$+$TiO_2$/$Fe_2O_3$
substrate flake+$TiO_2$/$Fe_2O_3$+$SiO_2$+$TiO_2$+$TiO_2$/$Fe_2O_3$
substrate flake+$TiO_2$/$Fe_2O_3$+$SiO_2$+$SnO_2$+$TiO_2$+$TiO_2$/$Fe_2O_3$
substrate flake+$TiO_2$/$Fe_2O_3$+$SiO_2$+$TiO_2$
substrate flake+$TiO_2$/$Fe_2O_3$+$SiO_2$+$SnO_2$+$TiO_2$
substrate flake+$TiO_2$/$Fe_2O_3$+$SiO_2$+$TiO_2$/$Fe_2O_3$
substrate flake+$TiO_2$+$SiO_2$+$Fe_3O_4$
substrate flake+$TiO_2$+$SiO_2$+$Cr_2O_3$
substrate flake+$Cr_2O_3$
substrate flake+$Fe_2O_3$+$SiO_2$+$TiO_2$/$Fe_2O_3$
substrate flake+$SiO_2$+$TiO_2$ (anatase)
substrate flake+$SiO_2$+$SnO_2$+$TiO_2$ (rutile)
substrate flake+$SiO_2$+$TiO_2$+alkaline-earth metal titanate
substrate flake+$SiO_2$+$SnO_2$+$TiO_2$+alkaline-earth metal titanate
substrate flake+$SiO_2$+$TiO_2$+$Fe_2O_3$
substrate flake+$SiO_2$+$SnO_2$+$TiO_2$+$Fe_2O_3$
substrate flake+$SiO_2$+$TiO_2$+$Fe_3O_4$
substrate flake+$SiO_2$+$SnO_2$+$TiO_2$+$Fe_3O_4$
substrate flake+$SiO_2$+$TiO_2$+$Cr_2O_3$
substrate flake+$SiO_2$+$SnO_2$+$TiO_2$+$Cr_2O_3$
substrate flake+$SiO_2$+$TiO_2$+Carmine Red
substrate flake+$SiO_2$+$SnO_2$+$TiO_2$+Carmine Red
substrate flake+$SiO_2$+$TiO_2$+Berlin Blue
substrate flake+$SiO_2$+$SnO_2$+$TiO_2$+Berlin Blue
substrate flake+$SiO_2$+$TiO_2$/$Fe_2O_3$
substrate flake+$SiO_2$+$SnO_2$+$TiO_2$/$Fe_2O_3$
substrate flake+$SiO_2$+$TiO_2$+$SiO_2$+$TiO_2$
substrate flake+$SiO_2$+$SnO_2$+$TiO_2$+$SiO_2$+$SnO_2$+$TiO_2$
substrate flake+$SiO_2$+$Fe_2O_3$
substrate flake+$SiO_2$+$Fe_3O_4$
substrate flake+$SiO_2$+$TiO_2$+$SiO_2$+$TiO_2$/$Fe_2O_3$
substrate flake+$SiO_2$+$SnO_2$+$TiO_2$+$SiO_2$+$TiO_2$/$Fe_2O_3$
substrate flake+$SiO_2$+$TiO_2$+$SiO_2$+$TiO_2$+$TiO_2$/$Fe_2O_3$
substrate flake+$SiO_2$+$SnO_2$+$TiO_2$+$SiO_2$+$TiO_2$+$TiO_2$/$Fe_2O_3$
substrate flake+$SiO_2$+$SnO_2$+$TiO_2$+$SiO_2$+$SnO_2$+$TiO_2$+$TiO_2$/$Fe_2O_3$
substrate flake+$SiO_2$+$TiO_2$/$Fe_2O_3$+$SiO_2$+$TiO_2$+$TiO_2$/$Fe_2O_3$
substrate flake+$SiO_2$+$TiO_2$/$Fe_2O_3$+$SiO_2$+$SnO_2$+$TiO_2$+$TiO_2$/$Fe_2O_3$
substrate flake+$SiO_2$+$TiO_2$/$Fe_2O_3$+$SiO_2$+$TiO_2$
substrate flake+$SiO_2$+$TiO_2$/$Fe_2O_3$+$SiO_2$+$SnO_2$+$TiO_2$
substrate flake+$SiO_2$+$TiO_2$/$Fe_2O_3$+$SiO_2$+$TiO_2$/$Fe_2O_3$
substrate flake+$SiO_2$+$TiO_2$+$SiO_2$+$TiO_2$/$Fe_2O_3$
substrate flake+$SiO_2$+$TiO_2$+$SiO_2$+$Fe_3O_4$
substrate flake+$SiO_2$+$TiO_2$+$SiO_2$+$Cr_2O_3$
substrate flake+$SiO_2$+$Cr_2O_3$
substrate flake+$SiO_2$+$Fe_2O_3$+$SiO_2$+$TiO_2$/$Fe_2O_3$
substrate flake+$TiO_2$ (anatase)+$SiO_2$ or
substrate flake+$SnO_2$+$TiO_2$ (rutile)+$SiO_2$.

11. The effect pigment according to claim 1, that is aftertreated with an organic and/or inorganic layer in order to increase light, water and weather stability.

12. A pigment composition comprising an effect pigment according to claim 1 and at least one absorbent, astringent, antimicrobial substance, antioxidant, antiperspirant, antifoaming agent, antidandruff active ingredient, antistatic, binder, biological additive, bleaching agent, chelating agent, deodorant, emollient, emulsifier, emulsion stabiliser, dye, humectant, film former, filler, odor substance, flavor substance, insect repellent, preservative, anticorrosion agent, cosmetic oil, solvent, oxidant, vegetable constituent, buffer substance, reducing agent, surfactant, propellant gas, opacifier, UV filter and UV absorber, denaturing agent, viscosity regulator, perfume or vitamin.

13. A pigment composition comprising one or more binders, optionally one or more additives and at least one effect pigment according to claim 1.

14. A dry preparation comprising at least one effect pigment according to claim 1.

15. In paints, automotive paints, industrial coatings, coatings, powder coatings, printing inks, plastics, button pastes, ceramic materials, glasses, colored seed, absorbers in the laser marking of plastics, glasses, cardboard, paper, absorbers in the laser welding of plastics, colored food or pharmaceutical products, colored coatings on food or pharmaceutical products, cosmetic formulations, or anti-counterfeiting-elements in documents of value comprising an effect pigment, the improvement wherein the effect pigment is one according to claim 1.

16. An effect pigment having a roundish flake-form substrate obtained by a process comprising grinding substrates in the form of flakes to form ground substrate flakes having a diameter of 50-200 µm, subsequently introducing ground substrate flakes into a comminution machine, adding water and/or an organic solvent, and a suspension formed in this way is treated mechanically in the comminution machine, during which the surface of the flakes is polished smooth and the mechanical loading of the substrate flakes is selected so that a permanent shear results in further gentle delamination of flakes and in smoothing of edges and surfaces and a particular-size distribution of 5-60 µm is achieved by a subsequent classification step in the form of a plurality of sedimentation steps, said effect pigment having a circular form factor of 1.2-2,
   wherein the flake-form substrate is synthetic mica flakes, natural mica flakes, $SiO_2$ flakes, $Al_2O_3$ flakes, glass flakes, iron oxide flakes, graphite flakes, $TiO_2$ flakes or mixtures thereof,
   wherein the high-refractive-index layer comprises at least one metal oxide, metal sulfide, iron titanate, iron oxide hydrate, titanium suboxide, $TiO_2$, BiOCl, $Ce_2O_3$, $Cr_2O_3$, COO, $Co_3O_4$, $Fe_2O_3$, $Fe_3O_4$, FeOOH, NiO, $SnO_2$, $VO_2$, $V_2O_3$, $ZrO_2$, ZnO, $CoAl_2O_4$, $BiVO_4$, $Ti_3O_5$, $Ti_2O_3$, TiO, $Ce_2S_3$, $MoS_2$ or mixtures or mixed phases of said compounds with one another; and
   wherein the roundish shape results in increased color saturation and hiding power compared with a non-roundish pigment with oblong shape and greater edge roughness.

17. A process for the preparation of an effect pigment according to claim 1, comprising grinding substrates in the form of lumps or coarse flakes to form substrate flakes having a diameter of 50-200 µm, subsequently introducing said flakes into a comminution machine, and adding water and/or an organic solvent, and treating a suspension thus formed mechanically for a number of hours in the comminution machine, during which the surface of the flakes is polished, maintaining mechanical loading of the substrate particles during comminution so that a permanent shear results in further gentle delamination of particles and in smoothing of the edges and surfaces and a narrowed particle-size distribution is achieved by a subsequent classification in the form of a plurality of sedimentations.

18. The process according to claim 17, wherein the narrowed particle-size distribution is 5-60 µm.

* * * * *